United States Patent
Torres et al.

(10) Patent No.: US 8,252,317 B2
(45) Date of Patent: Aug. 28, 2012

(54) METAL ALGINATE HYDROGEL AND ARTICLES THEREOF

(75) Inventors: Andrew Soliz Torres, Troy, NY (US); Peter John Bonitatibus, Jr., Saratoga Springs, NY (US)

(73) Assignee: General Electric Company, Niskayuna, NY (US)

( * ) Notice: Subject to any disclaimer, the term of this patent is extended or adjusted under 35 U.S.C. 154(b) by 699 days.

(21) Appl. No.: 12/393,101

(22) Filed: Feb. 26, 2009

(65) Prior Publication Data

US 2010/0216243 A1 Aug. 26, 2010

(51) Int. Cl.
*C07H 21/02* (2006.01)
*C07H 21/04* (2006.01)
*A61F 13/00* (2006.01)
*A61K 9/00* (2006.01)

(52) U.S. Cl. ........ 424/443; 424/447; 424/444; 424/445; 424/446; 424/448; 424/400

(58) Field of Classification Search ........................ None
See application file for complete search history.

(56) References Cited

U.S. PATENT DOCUMENTS

| | | | |
|---|---|---|---|
| 3,201,353 A * | 8/1965 | Corben | ........................ 428/402.2 |
| 4,806,355 A | 2/1989 | Goosen et al. | |
| 5,266,326 A | 11/1993 | Barry et al. | |
| 5,718,916 A | 2/1998 | Scherr | |
| 6,164,012 A | 12/2000 | Lechelt-Kunze et al. | |
| 6,497,902 B1 | 12/2002 | Ma | |
| 6,642,363 B1 | 11/2003 | Mooney et al. | |
| 7,128,929 B1 | 10/2006 | Scherr | |

FOREIGN PATENT DOCUMENTS

WO   2007127231 A2   11/2007

OTHER PUBLICATIONS

West et al., Physical properties of alginate hydrogels and their effects on in vitro follicle development, Biomaterials 28 (2007) 4439-4448.*
Bazhanov et al., Structure and electronic properties of zirconium and hafnium nitrides and oxynitrides, Journal of Applied Physics 97, 044108_2005_.*
Wayne Rosamond, Katherine Flegal, Gary Friday et al; "Heart Disease and Stroke Statistics—2007 Update"; Report From the American Heart Association Statistics Committee and Stroke Statistics Subcommittee; (Circulation. 2007;115:e69-e171.); © 2007 American Heart Association, Inc.
Amado LC, Saliaris AP, Schuleri KH, et al.; "Cardiac repair with intramyocardial injection of allogeneic mesenchymal stem cells after myocardial infarction"; Communicated by Victor A. McKusick, The Johns Hopkins University School of Medicine, Baltimore, MD, Jun. 2, 2005 (received for review Apr. 13, 2005); 8 pages.
Martin Rodriguez-Porcel, Todd J. Brinton, Ian Y. Chen, Olivier Gheysens, Jennifer Lyons, Fumiaki Ikeno, Jürgen K. Willmann, Lily Wu, Joseph C. Wu, Alan C Yeung, Paul Yock, and Sanjiv Sam Gambhir; "Reporter Gene Imaging Following Percutaneous Delivery in Swine"; Stanford University School of Medicine, Bio-X Program, Departments of Radiology and Bioengineering, The James H. Clark Center, 318 Campus Drive, Clark E150, Stanford, California 94305-5427 (Email: sgambhir@stanford.edu ); J Am Coll Cardiol, 2008.
Ranil De Silva, Luis F. Gutierrez, Amish N. Raval, Elliot R. McVeigh, Cengizhan Ozturk, and Robert J. Lederman; "X-Ray Fused With Magnetic Resonance Imaging (XFM) to Target Endomyocardial Injections"; Validation in a Swine Model of Myocardial Infarction; Received Nov. 3, 2005; revision received Sep. 19, 2006; accepted Sep. 22, 2006; Correspondence to Robert J. Lederman, MD, Cardiovascular Branch, Bldg 10, Room 2C713, Bethesda, MD 20892-1538; (Circulation. 2006;114:2342-2350.) © 2006 American.
Brad P Barnett, Aravind Arepally, Parag V Karmarkar, Di Qian, Wesley D Gilson, Piotr Walczak, Valerie Howland, Leo Lawler, Cal Lauzon, Matthias Stuber, Dara L Kraitchman and Jeff W M Bulte; "Magnetic resonance—guided, real-time targeted delivery and imaging of magnetocapsules immunoprotecting pancreatic islet cells"; Received Jan. 29; accepted Mar. 21; published online Jul. 29, 2007; doi:10.1038/nm1581; 6 pages.
B. P. Barnett, D. L. Kraitchman, C. Lauzon, C. A. Magee, P. Walczak, W. D. Gilson, A. Arepally and J. W. M. Bulte; "Radiopaque Alginate Microcapsules for X-ray Visualization and Immunoprotection of Cellular Therapeutics"; vol. 3, No. 5, 531-538; Received May 20; Publication Date (Web): Aug. 5, 2006.
G. Ciofani, V. Raffa, T. Pizzorusso, A. Menciassi and P. Dario; "Characterization of an alginate-based drug delivery system for neurological applications"; Received Jun. 6, 2007; received in revised form Oct. 3, 2007; accepted Oct. 16, 2007. published online Nov. 26, 2007; vol. 30, Issue 7, pp. 848-855 (Sep. 2008).

* cited by examiner

*Primary Examiner* — Jim Ketter
*Assistant Examiner* — Reza Ghafoorian
(74) *Attorney, Agent, or Firm* — Andrew J. Caruso

(57) ABSTRACT

The present invention provides novel metal alginates prepared from non-cross-linked alginate monomers such as sodium alginate and an aqueous solution of a group 4, 5, or 6 metal oxyhalide. The novel group 4, 5, and 6 metal alginates are useful in the preparation of cell culture supports, exhibit useful X-ray contrast properties, and exhibit unanticipated stability to standard autoclave conditions relative to known metal alginates such as calcium alginate. In general, the novel metal alginates provided by the present invention offer features and properties not observed in known metal alginates such as calcium or barium alginates.

14 Claims, No Drawings

METAL ALGINATE HYDROGEL AND ARTICLES THEREOF

BACKGROUND

This invention relates generally to cross-linked alginate monomers and more particularly to biocompatible alginate hydrogels.

Alginates form gels with most di- and trivalent metal salts. The alginate gels have many applications, including their use as an immobilization matrix for cell cultures, for in vitro culture media, as an injectable cell delivery vehicle, for immunoisolation-based therapies, and as enzyme immobilization substrates. Alginate hydrogels are very useful for application in cell-related studies due to their mild gelling condition, low diffusion constraints to cell nutrients, low inflammatory properties and biocompatibility. However, a significant limitation of alginate hydrogels utility is poor cell adhesion. Robust cell adhesion is required for cell attachment and long-term cell survival, particularly in mammalian cell systems.

An emerging need in various areas of biology and medicine is the development of cell culture materials exhibiting a combination of adequate cell adherence during cell growth and subsequent controlled cell release from the cell culture material when the cells are to be harvested. It would be highly desirable to provide new cell culture materials, which retain structure and functionality under sterilization conditions and thereafter, properties essential for various applications involving cell culture. Thus, the discovery of a cell culture material that is robust with respect to standard autoclave conditions, possesses excellent cell adhesion properties and controllable cell release characteristics represents a highly desirable goal.

BRIEF DESCRIPTION

In one aspect, the present invention provides, a metal alginate composition comprising structural units derived from a group 4, 5, or 6 metal oxyhalide and an alginate ligand.

In another aspect, the invention provides a metal alginate hydrogel comprising structural units derived from a group 4, 5, or 6 metal oxyhalide and an alginate ligand.

In yet another aspect, the present invention provides an article comprising a metal alginate hydrogel, wherein said metal alginate hydrogel comprises structural units derived from a group 4, 5, or 6 metal oxyhalide and an alginate ligand.

These and other features, aspects, and advantages of the present invention may be understood more readily by reference to the following detailed description.

DETAILED DESCRIPTION

Unless otherwise indicated, the article "a" refers to one or more than one of the word modified by the article "a." Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

As used herein, the term alginate refers to a copolymer comprising structural units derived from β-D-mannuronic acid and α-L-guluronic acid. Alginates are typically linear co-polymers comprising structural units derived from β-D-mannuronic acid and α-L-guluronic acid and occur naturally in various algae (such as *Laminaria japonica*) and bacteria. In certain instances, alginates are block copolymers comprised exclusively of structural units derived from β-D-mannuronic acid and α-L-guluronic acid. Alginates, which are block copolymers, may be random block copolymers or highly ordered block copolymers, for example a di-block copolymer comprising a single block of structural units derived from β-D-mannuronic acid and a single block of structural units derived from α-L-guluronic acid. The term alginate includes synthetic and semisynthetic copolymers comprising structural units derived from β-D-mannuronic acid and α-L-guluronic acid. Synthetic copolymers comprising structural units derived from β-D-mannuronic acid and α-L-guluronic acid are referred to herein as synthetic alginates. Correspondingly, semisynthetic copolymers comprising structural units derived from β-D-mannuronic acid and α-L-guluronic acid are referred to herein as semisynthetic alginates. The term semisynthetic alginate refers to a naturally occurring alginate which has been transformed chemically or biologically by man. For example, a naturally occurring alginate may be acetylated under Schotten Bauman conditions to produce an acetylated semisynthetic alginate, or epimerized in vitro using a mannuronan C-5 epimerase to produce a different semisynthetic alginate. As in many other areas of chemistry, the physical and biological properties of alginates may be highly dependent upon structure, and while some structure-activity relations have been defined for alginates, countless alginate compositions and their properties remain unexplored. It is been proposed that alginates with higher guluronic acid levels and larger block structures typically exhibit stronger interaction with calcium ions and hence stronger gel strength.

As used herein the term alginate ligand refers to an alginate which is bound to one or more metal centers. In various embodiments of the present invention the alginate ligands are bound to a metal center comprising a group 4, 5, or 6 metal. The metal center comprising a group 4, 5, or 6 metal to which the alginate ligand is bound may be a single metal ion, or a more complex structure such as a metal cluster comprising a plurality of group 4, 5, or 6 metal ions and oxygen atoms.

As used herein the term alginate hydrogel refers to a metal alginate composition which is a network of alginate polymer chains formed by contacting a water soluble alginate polymer with a crosslinking agent, for example a metal oxyhalide, in an aqueous medium. Alginate hydrogels are typically water insoluble, and may comprise substantial amounts of water.

In one embodiment, the present invention provides a metal alginate composition comprising structural units derived from a group 4, 5, or 6 metal oxyhalide and an alginate ligand. Thus, the metal alginate compositions provided by the present invention comprise an alginate ligand bound to a metal center having a structure which is derived from a metal oxyhalide of a group 4, 5, or 6 metal. The group 4, 5 and 6 metals include the transition metals titanium, zirconium and hafnium (group 4); vanadium, niobium, and tantalum (group 5); and chromium, molybdenum, and tungsten (group 6). These structural units derived from a group 4, 5, or 6 metal oxyhalide necessarily comprise a group 4, 5, or 6 metal and serve as sites which may serve crosslinks between individual alginate chains and to form a network structure. As noted, the structural units derived from the metal oxyhalide may have a variety of structures and compositions within a metal alginate composition varying from a single metal ion bound to one or more alginate ligands, to a metal-containing cluster comprising a plurality of metal ions and oxygen atoms, where the metal-containing cluster being bound to one or more alginate ligands. As will be appreciated by those of ordinary skill in the art, the nature (i.e. composition and structure) of the structural units derived from the metal oxyhalide may in certain embodiments be highly dependent upon the conditions under which the metal alginate composition is formed. In this regard, the metal oxyhalides are especially well suited to serve as precursors to metal alginate compositions provided by the present invention owing to a combination of appropriate reactivity and water solubility.

In one embodiment, the metal oxyhalide is selected from the group consisting of the group 4 metal oxyhalides, the group 5 metal oxyhalides, and the group 6 metal oxyhalides. Group 4 metal oxyhalides include the titanium oxyhalides, zirconium oxyhalides, and hafnium oxyhalides. Titanium oxyhalides are illustrated by $TiOF_2$, $TiOCl_2$, and $TiOBr_2$ Zirconium oxyhalides are illustrated by $ZrOF_2$, $ZrOCl_2$, and $ZrOBr_2$. Hafnium oxyhalides are illustrated by $HfOF_2$, $HfOCl_2$, and $HfOBr_2$. In an alternate embodiment, the metal oxyhalide is selected from the group consisting of the group 5 metal oxyhalides. Group 5 metal oxyhalide include the vanadium oxyhalides, niobium oxyhalides, and tantalum oxyhalides. Vanadium oxyhalides are illustrated by $VOF_3$, $VOCl_3$, and $VOBr_3$. Niobium oxyhalides are illustrated by $NbOF_3$, $NbOCl_3$ (CAS Reg. No. 13597-20-1), and $NbOBr_3$. Tantalum oxyhalides are illustrated by $TaOF_3$, $TaOCl_3$, and $TaOBr_3$. Group 6 metal oxyhalide include the chromium oxyhalides, molybdenum oxyhalides, and tungsten oxyhalides. Chromium oxyhalides are illustrated by $CrOF_4$, $CrOCl_4$, and $CrOBr_4$. Molybdenum oxyhalides are illustrated by $MoOF_4$, $MoOCl_4$, and $MoOBr_4$. Tungsten oxyhalides are illustrated by $WOF_4$, $WOCl_4$ (CAS Reg. No. 13520-78-0), and $WOBr_4$.

In one embodiment, the metal oxyhalide is selected from the group consisting of titanium oxyhalides, zirconium oxyhalides, and hafnium oxyhalides. In an alternate embodiment, the metal oxyhalide is zirconium oxychloride, hafnium oxychloride, or a combination thereof. In instances in which the metal oxyhalide comprises a combination of two or more metal oxyhalides, the metal alginate composition provided by the present invention comprises structural units derived from each of the metal oxyhalides. In one embodiment, the metal oxyhalide is zirconium oxychloride and the metal alginate composition provided by the present invention comprises structural units derived from zirconium oxychloride.

As noted, the metal alginate compositions provided by the present invention comprises an alginate ligand having a number average molecular weight as determined by gel permeation chromatography in a range from about 5 kilodaltons (kda) to about 500 kilodaltons. In one embodiment, the present invention provides a metal alginate composition comprising alginate ligands bound to structural units derived from a group 4, 5, or 6 metal oxyhalide, said alginate ligands comprising structural units derived from β-D-mannuronic acid and structural units derived from α-L-guluronic acid, said alginate ligands having a number average molecular weight as determined by gel permeation chromatography in a range from about 5 kilodaltons (kda) to about 500 kilodaltons. In one embodiment, the present invention provides an alginate composition wherein the alginate ligand comprises oligomeric blocks comprising structural units derived from β-D-mannuronic acid and oligomeric blocks comprising structural units derived from α-L-guluronic acid. Oligomeric blocks are defined herein as blocks of a copolymer having a number average molecular weight of less than 5 kilodaltons. In one embodiment, the alginate ligand is a block copolymer comprising discrete oligomeric blocks comprised of β-D-mannuronic acid residues and discrete oligomeric blocks comprised of α-L-guluronic acid residues. As used herein, a block is oligomeric when it is characterized by a block length corresponding to a number average molecular weight of less than 2 kilodaltons. In one embodiment, the present invention provides a metal alginate composition comprising a polydisperse alginate ligand wherein the polydispersity ($M_w/M_n$) of the alginate ligand as measured by gel permeation chromatography is in a range from about 1.4 to about 6.0. In one embodiment, the present invention provides a metal alginate composition comprising structural units derived from a group 4, 5, or 6 metal oxyhalide and an alginate ligand having a weight average molecular weight in a range from about 10 kilodaltons to about 100,000 kilodaltons.

As noted, alginates comprise structural units derived from β-D-mannuronic acid (mannuroate units) and α-L-guluronic acid (guluronate units). In one embodiment, the present invention provides a metal alginate composition wherein the alginate ligand is characterized by a weight ratio of mannuronate to guluronate in a range from about 0.001 to about 1000. In an alternate embodiment, the present invention provides a metal alginate composition wherein the alginate ligand is characterized by a weight ratio of mannuronate to guluronate in a range from about 0.01 to about 100. In yet another embodiment, the present invention provides a metal alginate composition wherein the alginate ligand is characterized by a weight ratio of mannuronate to guluronate in a range from about 0.1 to about 10. In still yet another embodiment, the present invention provides a metal alginate composition wherein the alginate ligand is characterized by a weight ratio of mannuronate to guluronate in a range from about 0.5 to about 1. The relative amounts of β-D-mannuronic acid and α-L-guluronic acid present in the alginate ligands and hence the weight ratio of the mannuroate units to guluronate units, is believed to play a role in determining the physical structure and properties of the metal alginates provided by the present invention. Properties such as gel-strength, heat resistance, cell affinity, bead-forming efficiency, salt resistance, on demand dissolution are all believed to be at least somewhat dependent on the structure and composition of the alginate ligand. In certain embodiments, and for certain applications a higher proportion of structural units derived from α-L-guluronic acid may be desirable. Alternatively, a higher proportion of structural units derived from β-D-mannuronic acid at times may be desirable.

As noted, in one embodiment, the present invention provides a metal alginate composition which is an alginate hydrogel. Those of ordinary skill in the art will understand that as used herein, an alginate hydrogel is a class of alginate compositions which are formed by contacting a water soluble alginate with at least one of a group 4, 5, or 6 metal oxyhalide which serves as a crosslinking agent, in an aqueous medium. The alginate hydrogels provided by the present invention are typically water insoluble, may comprise substantial amounts of water, and may be prepared easily in the form of beads comprising the alginate hydrogel. Experimental details and guidance for the preparation of the alginate hydrogels provided by the present invention are given in the experimental section of this disclosure. In a specific non-limiting embodiment, the present invention provides an alginate hydrogel comprising structural units derived from zirconium oxychloride, and an alginate ligand.

Among the many advantages presented by the alginate compositions provided by the present invention is a substantial and useful degree of radio-opacity experimentally observed in the alginate hydrogels disclosed herein. Thus in various embodiments, the metal alginate hydrogel is said to be radio-opaque. Radio-opacity is a property of a material, whereby the material obstructs or is non-transparent to the passage of electromagnetic waves at certain wavelengths, particularly X-rays. This obstruction of or non-transparency to electromagnetic waves such as X-rays, permits the imaging of articles comprising the metal alginates provided by the present invention using X-ray imaging techniques.

A further embodiment, the present invention provides an article comprising a metal alginate composition of the present invention. In some embodiments, the article comprising the metal alginate composition is a cell carrier support. In various embodiments, the present invention provides an article comprising a metal alginate composition of the invention, which is substantially radio-opaque. By substantially radio-opaque it is meant that the article is sufficiently radio-opaque to observable using an x-ray imaging technique. In one embodiment, the present invention provides a cell carrier support comprising a metal alginate composition of the invention wherein the cell carrier support is substantially radio-opaque.

A cell carrier support, as referred to herein, is a substrate for adhering and culturing cells. In a specific embodiment, the present invention provides a cell carrier support for cell growth, wherein the cell carrier support is configured as a cell carrier bead comprising a radio-opaque metal alginate composition of the invention. In another embodiment, the present invention provides a cell carrier support configured as a cell carrier scaffold comprising a radio-opaque metal alginate of the invention. Cell carrier beads and cell carrier scaffolds can be of a wide variety of shapes and sizes. In some embodiments, the cell carrier support is a bead having a diameter greater than about 500 nm. Suitable examples of cell carrier supports, include, but are not limited to discs, Petri dishes, plates, fibers, and particles. It is believed that, owing to their outstanding physical and cell-binding properties, the metal alginate compositions provided by the present invention may be employed in an even wider variety of cell carrier supports than those illustrated above. In one embodiment, the present invention provides a cell carrier support that is configured as a mesh. In an alternate embodiment, the present invention provides a cell carrier support that is configured as a web.

In certain embodiments, the metal alginate composition provided by the present invention dissolves upon treatment with a solution containing a metal chelating agent such as ethylenediamine tetraacetic acid (EDTA). In a variety of embodiments in which the metal alginate composition of the present invention is configured as a cell carrier support, the cell carrier support may be rapidly dissolved in an aqueous solution containing a metal chelating agent such as EDTA. Those having ordinary skill in the art will appreciate that when a cell carrier support comprising a cell culture is treated with an aqueous solution containing a metal chelating agent capable of dissolving the metal alginate composition, such treatment effectively releases the cells of the cell culture from the cell carrier support as the cell carrier support is dissolved.

In various embodiments, the metal alginates compositions provided by the present invention have been found to exhibit enhanced resistance to buffer solutions and other ionic solutions. For example, the metal alginates compositions of the present invention have been found to exhibit a surprising degree of resistance to attack by aqueous solutions containing phosphate ions. Known metal alginates typically lack such resistance and dissolve readily in solutions containing phosphate ions. Thus, in one embodiment, the present invention provides an article comprising a metal alginate composition of the present invention, said article being resistant to ionic solutions, for example a solution comprising phosphate ions. It has also been discovered that under certain conditions it is possible to effect cell release from a cell carrier support comprising a metal alginate composition provided by the present invention, upon treatment with an aqueous ionic solution comprising phosphate ions without destroying the structural integrity of the cell carrier support. In one embodiment, cells can be released from the support in the presence of high concentrations of phosphate ions without affecting the structural integrity of the support.

The physical characteristics of the metal alginate compositions provided by the present invention are believed to depend on inter-chain interactions occasioned by the presence of structural units derived from a group 4, 5, or 6 metal oxyhalide. It is convenient to consider the metal oxyhalide derived structural units as reversibly cross-linking individual alginate chains. It is believed that cross-linking provides the metal alginate compositions of the present invention with advantageous physical characteristics such as toughness and elasticity, which make them especially suitable for use in cell-culture applications. In addition, it is believed that the structure of the metal alginate compositions of the present invention enhances cell adhesion relative to known metal alginate compositions, and that successful cell adhesion to a cell carrier support comprised of a metal alginate composition of the present invention can be achieved without the use of cell-adhesion promoting treatments.

Notwithstanding the foregoing, in certain embodiments it may be advantageous to employ techniques which further enhance cell adhesion to cell carrier supports provided by the present invention. Thus, in one embodiment, a cell carrier support comprising structural units derived from a zirconium oxyhalide and an alginate ligand is treated with ACES (N-2-acetamido-2-aminoethane sulfonate) to modify the cell carrier support surface and thereby promote cell adhesion. The reagent ACES contains a primary amine group and is on that basis thought to enhance cell adhesion. For cell carrier supports comprised chiefly of calcium alginate and water, surface modification by ACES or a poly-L-lysine is necessary to achieve useful levels of cell binding as well to achieve useful levels of cell-growth and cell viability. In sharp contrast to the behavior of the known calcium alginates, cell carrier supports comprising the metal alginate compositions of the present invention, have been shown not to require such surface treatments in order to achieve useful levels of cell adhesion, cell growth and cell viability.

A method of making a metal alginate hydrogel is disclosed in one or more embodiments of the present invention. The method includes the steps of mixing a solution of a group 4, 5, or 6 metal oxyhalide with a water soluble alginate salt, such as sodium alginate, and isolating the precipitated metal alginate. In one embodiment, the solution of the metal oxyhalide comprises an initial concentration of zirconium oxychloride in an amount corresponding to from about 1.1 percent by weight (wt %) to about 3.6 wt % based on a total weight of the solution, and the concentration of the water soluble alginate is in a range from about 1 wt % to about 1.5 wt %.

EXPERIMENTAL PART

Practice of the invention will be more fully understood from the following examples, which are presented herein for illustration only and should not be construed as limiting the invention in any way.

General Methods: Bead Synthesis and Characterization

Materials: Zirconium (IV) dichloride oxide hydrate salt ($ZrOCl_2$) and Hafnium (IV) dichloride oxide hydrate salt ($HfOCl_2$) were obtained from Strem Chemicals and used without further purification. Alginic acid and sodium salt of alginic acid from brown algae were obtained from Fluka Chemie AG (product code 71240). Deionized water was used for all syntheses.

Beads comprising the metal alginate compositions of the invention were prepared by addition of a sodium alginate solution comprising from about 1 to about 1.5 percent by weight (wt %) sodium alginate in water to an aqueous solution of zirconyl oxychloride ($ZrOCl_2$) or hafnyl oxychloride ($HfClO_2$) having a nominal concentration of from about 1.1 to about 3.6 percent by weight of $ZrOCl_2$ or $HfClO_2$. In all bead-forming experiments, alginate-droplets were brought into contact with zirconyl (or hafnyl) aqueous baths at room temperature. Three to five minutes were granted to allow for the cross-linking of sodium alginate by the zirconium or hafnium species present. Beads were isolated by decantation after allowing them to "set" in a bead-forming aqueous acidic $ZrOCl_2$ or $HfClO_2$ bath. Beads were purified by thorough washing with sterile saline solution (150 mM NaCl). Beads were stored in saline solution until used.

In an exemplary procedure, a 1.25 wt % solution of sodium alginate was added dropwise to an undisturbed aqueous solution nominally containing 3 wt % $ZrOCl_2$ in a glass beaker to provide beads comprising a metal alginate comprising structural units derived from zirconium oxychloride and an alginate ligand. In a second exemplary procedure, a sodium alginate solution having a concentration of 1.25 wt %, was added dropwise to a two phase mixture contained in a plastic beaker, the mixture comprising an upper toluene phase and a lower aqueous phase prepared from zirconium oxychloride or hafnium oxychloride and water and nominally comprising 3 wt % of zirconium or hafnium. Bead morphology appeared to be more consistent using the modified procedure. It was observed in the modified two-phase procedure that droplets of the 1.25 wt % sodium alginate solution moved quickly to the edge of the toluene meniscus and traveled along the edge of the beaker before coming into contact with the aqueous solution.

Bead synthesis by the methods described herein were reproducible and product beads of about 0.5 cm in diameter and about 0.1 cm in thickness having a disc-like shape and having a volume of about 0.0196 cubic centimeters were typically obtained. The resultant beads were observed to exhibit a greater degree of stiffness than had been previously observed beads comprising calcium alginates. It was further observed that the morphology of beads produced using the second exemplary procedure was more consistent than that observed using the first exemplary procedure.

Immediately after synthesis, the beads were washed using saline in a volume five times greater than the volume of aqueous zirconyl or hafnyl oxychloride bath used to produce the beads. Washing facilitated the removal of any unreacted zirconyl or hafnyl chloride components not consumed by sodium alginate. To determine the complete removal of any unreacted components, the pH of the solution containing the beads was monitored. Impurities in the solution from the synthesis would result in a pH below 5 in standard saline solution (0.9% NaCl in water).

Table 1 presents the results of elemental analysis of beads formed by adding a solution of sodium alginate dropwise via a syringe into a bath of $ZrOCl_2$ (first exemplary procedure). As is evident from Table 1, the beads contained roughly 0.1 mg zirconium per bead, which is calculated to be about 56 mM zirconium per bead volume. Similar results with beads comprising structural units derived from hafnium oxychloride and an alginate ligand. Thus, addition of a sodium alginate solution to an aqueous solution of $HfOCl_2$ as in the first exemplary procedure afforded beads comprising the hafnium metal alginate hydrogel which were of comparable dimensions to the beads comprising the zirconium metal alginate hydrogel analyzed in Table 1.

TABLE 1

ELEMENTAL ANALYSIS OF SINGLE BEADS COMPRISING ZIRCONIUM METAL ALGINATE

| Entry | Weight Zirconium found | +/− Error |
|---|---|---|
| Bead 1 | 0.097 mg | 0.007 mg |
| Bead 2 | 0.126 mg | 0.007 mg |
| Bead 3 | 0.106 mg | 0.007 mg |

Bead Imaging

To test the contrast levels provided by these materials under standard X-ray computed tomography conditions, beads comprising structural units derived from either zirconium oxychloride and an alginate ligand or hafnium oxychloride and an alginate ligand were imaged as bead dispersions in saline solution contained in 6 well plates. Beads comprising the hafnium metal alginates and beads comprising the zirconium metal alginate were clearly visible in these scans and contrast measurements on a calibrated CT showed that bead contrast levels were between 700-800 HU (Hounsfeld units) at 80 kV.

Dye Release from Beads

Sample beads were produced by drop-wise addition of a 1 wt % sodium alginate solution to a 50 ml of 1.14 wt % $ZrOCl_2$ solution. The sodium alginate solution contained a drop of red dye #40 (6-hydroxy-5-((2-methoxy-5-methyl-4-sulfophenyl)azo)-2-naphthalenesulfonic acid). The red dye was thereby incorporated into the beads comprising the metal alginate.

An alternate means of attachment of a dye to a bead comprising a metal alginate was as follows. Beads comprising a metal alginate hydrogel were contacted with red food coloring (disodium 6-hydroxy-5-((2-methoxy-5-methyl-4-sulfophenyl)azo)-2-naphthalene-sulfonate) in either saline or deionized water (DI water) which resulted in attachment of the dye to the bead. Red beads were isolated after several minutes and thoroughly washed with DI water and saline. Beads comprising dye were shown to maintain integrity and hold the red color for several months. Red dyes typically have sulfonate groups which are believed to interact with cationic surfaces and to form coordinate covalent bonds with strongly electrophilic metal centers such as $Zr^{4+}$ and $Hf^{4+}$.

During the course of these studies it was discovered that treatment of dye-containing beads with a relatively strong inorganic nucleophile such as phosphate resulted in release of the dye from the bead without affecting the overall structural integrity of the bead. It is believed that phosphate is a sufficiently strong nucleophile to displace the more weakly nucleophilic dye moieties from zirconium and hafnium cation centers in the metal alginate. The metal alginates of the invention show a surprising level of resistance to attack by phosphate ion. In one experiment red dye-containing beads were placed into a phosphate buffered saline (PBS) (10 mM phosphate ion), appeared to be depleted of color entirely over a short period of time (minutes to hours) but the beads maintained structural integrity. This property of easy dye release from a bead while maintaining the structural integrity of the bead was observed in beads comprising structural units derived from zirconium oxychloride and sodium alginate as well as in beads comprising structural units derived from hafnium oxychloride and sodium alginate.

The release of the dye and the retention of the structural integrity of the bead stand in stark contrast to known properties of calcium cross-linked alginates which lose structural integrity when exposed to a phosphate buffer solution. It is believed that metal alginates of the invention comprising structural units derived from a group 4, 5, or 6 metal oxyhalide will exhibit substantial resistance to phosphate ion and beads comprising such metal alginates will maintain structural integrity in phosphate buffer solutions.

Cell Viability, Cell Proliferation and Count.

Materials: 96-well tissue culture grade flat bottom plates were obtained from Falcon BD (Cat# 353072), Costar 96-well Ultra Low Attachment Plates were obtained from Corning (Cat#3473), CHO-K1 (Chinese Hamster Ovary-K1) cells were obtained from ATCC (Cat# CCL-61), F-12 Ham Media was obtained from Invitrogen (Cat#31765-092) and Ham Media containing 10% FBS (Hyclone Cat #SH30070.03) and 1× Penicillin-Streptomycin was obtained from Invitrogen (Cat#15140-155), 10× Stock of Scaffold Reagent in Water or PBS was from Invitrogen (Cat#10010-049). The scaffold reagent was dissolved in water and the salt concentration was adjusted to 1×PBS using 10×PBS. Cell Proliferation WST-1 reagent was from Roche Applied Science (Cat#11644807001).

The concentrations of zirconyl ion and alginate were varied in a limited way and then binding of resulting beads to mammalian cells was tested. Dropwise addition of a 1.25wt % sodium alginate solution to an aqueous bath of 3wt % (nominal concentration) $ZrOCl_2$ provided beads comprising the zirconium metal alginate which were found suitable for cell binding and growth. CHO-K1 cells added in suspension to unmodified zirconyl alginate beads adhered to the surface of the beads and grew to confluence. Cell morphology was found to comparable to what is normally achieved in standard cell culture media. The excellent cell binding and cell proliferation results obtained with unmodified beads comprising the metal alginate compositions provided by the present invention stand in sharp contrast to unmodified calcium alginate beads which do not bind cells to any significant level and require addition of cationic groups to support cell binding and growth Cell viability experiments were conducted to evaluate cell binding and growth on cell carrier beads comprising the zirconium metal alginates provided by the present invention. Cells were added in suspension to the beads contained in a 96 well plate under sterile conditions and allowed to attach and grow under normal cell culture conditions. After the cells reached a high density on the carriers, the cells were released by addition of 5 mM EDTA (ethylenediamine tetraacetic acid). The viability of these cells was evaluated using a dye, WST-1 ("water soluble tetrazoium 1") that undergoes a color change in viable cells as the tetrazolium dye is reduced to formazan by mitochondrial succinate-tetrazolium reductase. Cells were monitored at 450 nm on a UV plate reader after incubating the released cells for one hour in the presence of the WST-1 dye. The number of viable cells was linearly correlated with the increase in absorbance at 450 nm above background, where the background was taken to be cell culture media containing cells.

CHO cells were grown to exponential phase in 'Full F-12 Ham media' containing Penicillin-Streptomycin in tissue culture incubator. The cells were placed in a plate washed once with PBS, followed by addition of 3 ml of 0.05% Trypsin and then incubated for 5 min at 37° C. Trypsin was inactivated and washed with full media, and finally resuspended in the F-12 Ham media. Zirconyl alginate beads were soaked in a solution of 1× phosphate-buffered saline and then added into individual wells of ultra-low attachment 96 well plates in triplicate. Calcium alginate beads and media alone were used as controls. Suspension of CHO-K1 cells at density of 20,000 cells/ml in fresh medium was added to each well at volume of 100 uL per well. Cell suspensions added to zirconyl alginate beads were incubated overnight for attaching cells on the beads. Twenty four hours later, old media and dead cells were removed and 100 uL of fresh media was added to each well. Cells were observed for at least 72 hours as cells reached >90% confluence on beads.

Cell release was performed by incubating the beads in 100 uL of full cell culture media with 5 mM EDTA at 37 degrees C. for 10 minutes. Following release of high-density cells, 100 uL of cells in media were transferred to new wells without the beads and WST-1 reagent (10 uL) was added to each well containing cell suspension. After 1 hour of incubation with WST-1 reagent under normal cell culture conditions, absorbance of samples was measured using microplate reader at 450 nm with a reference wavelength at 620 nm.

Viability assays were performed on the sample beads with cells to determine the rate of differentiation of cells in normal cell culture conditions. After 24 hours of seeding with 10000 cells per bead, the activity was roughly equivalent to standard 96 well values. Table 2 shows that after 72 hours of seeding, there is a measurable increase in activity which indicates the increased cell growth on zirconium alginate beads compared to the cell growth on calcium alginate beads. These results are consistent with respect to the media alone, which was treated as a control for the samples where cells are grown on zirconyl alginate beads or calcium alginate beads, indicating cell growth and differentiation.

TABLE 2

VIABILITY ASSAY RESULTS WITH WST-1 CELL PROLIFERATION REAGENT.

| Samples | Absorbance at $A_{450\,nm}$ | SD (+/−) |
|---|---|---|
| Media | 0.062 | 0.002 |
| Zr Alginate | 0.084 | 0.008 |
| Ca Alginate with CHO cells | 0.093 | 0.008 |
| Zr Alginate with CHO cells | 0.886 | 0.053 |

Because these beads were inherently stiffer and resistant to degradation by ions such as phosphate, testing was done to determine whether standard autoclave conditions would disrupt the beads since calcium alginate is not resistant to this sterilization procedure. Attachment and growth of two different cell lines (CHO-K1 and MRC-5) on non-autoclaved and autoclaved zirconyl alginate beads were compared by micrographic analysis. Autoclave conditions of 121 degrees Celsius for 15 minutes did not physically disrupt zirconyl beads and did not impact the ability of the zirconyl beads to bind and support cells. The result with the MRC-5 fibroblast cell line was particularly significant because the cells were found to be elongated and represent a similar phenotype to mesenchymal stem cells. The autoclaving had no impact on cell morphology for the cells grown on zirconium alginate beads.

The foregoing examples are merely illustrative, serving to illustrate only some of the features of the invention. The appended claims are intended to claim the invention as broadly as it has been conceived and the examples herein presented are illustrative of selected embodiments from a manifold of all possible embodiments. Accordingly, it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied; those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

The invention claimed is:

1. A metal alginate composition comprising:
   zirconium, hafnium, or a combination thereof; and
   an alginate ligand comprising one or more oligomeric blocks comprising D-mannuronate residues, and one or more oligomeric blocks of L-guluronate residues, wherein a weight ratio of mannuronate to guluronate in the alginate ligand is in a range from 0.5 to 1.0.

2. The metal alginate of claim 1, comprising: zirconium.

3. The metal alginate of claim 1, wherein the alginate ligand has a number average molecular weight in a range from about 5 kilodalton to about 500 kilodalton as determined by gel permeation chromatography.

4. A metal alginate hydrogel comprising:
   zirconium, and
   an alginate ligand comprising one or more oligomeric blocks comprising D-mannuronate residues, and one or more oligomeric blocks of L-guluronate residues and wherein a weight ratio of mannuronate to guluronate in the alginate ligand is in a range from 0.5 to 1.0.

5. An article comprising a metal alginate hydrogel, said metal alginate comprising:
   zirconium, hafnium, or a combination thereof; and
   an alginate ligand comprising one or more oligomeric blocks comprising D-mannuronate residues, and one or more oligomeric blocks of L-guluronate residues and wherein a weight ratio of mannuronate to guluronate in the alginate ligand is in a range from 0.5 to 1.0.

6. The article of claim 5, which is a cell carrier support.

7. The cell carrier support of claim 6, wherein the support is a bead with a diameter greater than 500 nm.

8. A metal alginate composition comprising:
   zirconium, hafnium or combinations thereof; and
   an alginate ligand having a weight average molecular weight in a range from about 10 kilodaltons to about 100,000 kilodaltons, wherein a weight ratio of mannuronate to guluronate in the alginate ligand is in a range from 0.5 to 1.0.

9. The metal alginate composition according to claim 8, wherein said alginate ligand is a naturally occurring alginate.

10. The metal alginate composition according to claim 8, wherein said alginate ligand is a semi-synthetic alginate.

11. The metal alginate composition according to claim 8, wherein the alginate ligand has a polydispersity in a range from about 1.4 to about 6.0.

12. The metal alginate composition according to claim 8, comprising: zirconium.

13. The metal alginate composition according to claim 8, comprising: hafnium.

14. A cell carrier support comprising the metal alginate composition of claim 8.

* * * * *